United States Patent [19]
Kim et al.

[11] Patent Number: 6,090,976
[45] Date of Patent: Jul. 18, 2000

[54] METHOD FOR PREPARATION 3-(HYDROXYPHENYLPHOSPHINYL)-PROPANOIC ACID

[75] Inventors: Jong Hee Kim; Dae Woo Ihm; Soo Sung Lee, all of Seoul, Rep. of Korea

[73] Assignee: Saehan Industries Incorporation, Kyongsangbuk-Do, Rep. of Korea

[21] Appl. No.: 09/414,934

[22] Filed: Oct. 12, 1999

[51] Int. Cl.$^7$ .................................................. C07F 9/30
[52] U.S. Cl. ........................................................ 562/24
[58] Field of Search .................................................. 562/24

[56] References Cited

U.S. PATENT DOCUMENTS

| | | | |
|---|---|---|---|
| 4,769,182 | 9/1988 | Hazen | 562/24 |
| 5,334,760 | 8/1994 | Wachi et al. | 562/24 X |
| 5,349,069 | 9/1994 | Thottahil et al. | 562/24 X |

Primary Examiner—Paul F. Shaver
Attorney, Agent, or Firm—Harrison & Egbert

[57] ABSTRACT

Disclosed is a method for the preparation of 3-(hydroxyphenylphosphinyl)-propanoic acid which is commonly used as a flame retardant for polyester resins. The preparation of 3-(hydroxyphenylphosphinyl)-propanoic acid is attained by the condensation of phenylphosphonous dichloride and acrylic acid and the hydrolysis of the condensate. In the condensation, the mole ratio of phenylphosphonous dichloride to acrylic acid is within the range of 1:1.1 to 1:1.25. Under a pressure of greater than 1 atm, acrylic acid is added at 65~110°C. at an amount more by 10~25 mole % than that of phenylphosphonous dichloride and the condensation is carried out at a temperature of 70~100° C. under at greater than 1 atm, to produce 3-(hydroxyphenylphosphinyl)-propanoic acid at high yields with desired color.

2 Claims, No Drawings

METHOD FOR PREPARATION 3-(HYDROXYPHENYLPHOSPHINYL)-PROPANOIC ACID

BACKGROUND OF THE INVENTION

1. Field of the Invention

The present invention relates to a method for preparing 3-(hydroxyphenylphosphinyl)-propanoic acid. 3-(hydroxyphenylphosphinyl)-propanoic acid, which is commonly used as a flame retardant for polyester resins, is generally prepared by the condensation of phenylphosphonous dichloride and acrylic acid, followed by the hydrolysis of the condensate, 3-(chlorophenylphosphinyl)-propionylchloride, as shown in the following reaction formula I:

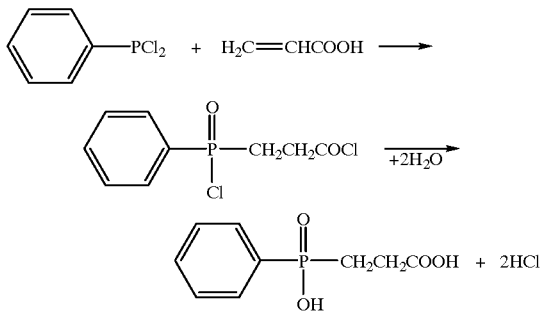

2. Description of the Prior Art

Pudovik et al. reported the above procedure in the Russian Journal of Organic Chemistry (Vol. 137, pp. 423–427) in 1967. Since then, there have been disclosed a number of improved procedures which could increase the production yield by controlling a reactant mole fraction or reaction temperature. For example, U.S. Pat. No. 4,081,463 (Birum et al.) proposes a method in which acrylic acid was used at an amount more by 25~45 mol % (more preferably 30~40 mol %) than that of phenylphosphonous dichloride, insisting that the production yield can be increased by using excess acrylic acid because a portion of phenylphosphonous dichloride remains unreacted when these reactants are present at the same equivalent. However, this method is problematic in that not only the reactant is wasted due to the excess of acrylic acid, but also the production yield is not increased to the is satisfactory extent. Another reference directed to the preparation of 3-(hydroxyphenylphosphinyl)-propanoic acid is found in U.S. Pat. No. 4,769,182, yielded to Hazen. It discloses that the object compound can be produced at high production yields by using acrylic acid at a relatively small amount, but greater by 5~10 mol % than that of phenylphosphonous dichloride and maintaining the reaction temperature at 115~150 ° C. during the reaction of the reactants. In the above-cited patent, Hazen insisted that acrylic acid was not consumed nor converted into an unreactable material, but converted into certain acrylic acid derivatives which were then reacted with remaining phenylphosphonous dichloride at the elevated reaction temperature, which led to an improvement in the production yield. However, despite the enhanced production yield, this method suffers from a weakness in that the effect of excess acrylic acid is abated because acrylic acid used in the reaction is self-condensed or boiled to vaporize owing to the high temperature.

Flame-retardant, 3-(hydroxyphenylphosphinyl)-propanoic acid-containing polyester is generally used for fibers such as curtains, coverlets and night dresses. One of the factors which have significant influence on the quality of these fiber products is color. The colors of the products are partly determined by the color of the polyester. Accordingly, the color of 3-(hydroxyphenylphosphinyl)-propanoic acid, which is added to provide flame retardation for polyester, is very important in determining the colors of final products.

As for 3-(hydroxyphenylphosphinyl)-propanoic acid prepared by the Hazen's method, it is slightly yellowish.

SUMMARY OF THE INVENTION

With this background in mind, the present invention solves the problems of prior arts, and has an object of providing a method for preparing 3-(hydroxyphenylphosphinyl)-propanoic acid of desired color at high yields.

Based on the present invention, the above object could be accomplished by a provision of a method for preparing 3-(hydroxyphenylphosphinyl)-propanoic acid by the condensation of phenylphosphonous dichloride and acrylic acid and the hydrolysis of the condensate, in which, under a pressure of greater than 1 atm, acrylic acid is added at 65~110° C. at an amount more by 10~25 mole % than that of phenylphosphonous dichloride and the condensation is carried out at a temperature of 70~100° C. under a pressure greater than 1 atm.

DETAILED DESCRIPTION OF THE INVENTION

In preparing 3-(hydroxyphenylphosphinyl)-propanoic acid from phenylphosphonous dichloride and acrylic acid through condensation reaction and hydrolysis in succession, the present invention is characterized in that, under a pressure of greater than 1 atm, acrylic acid is added at 65~110° C. at an amount more by 10~25 mole % than that of phenylphosphonous dichloride and a condensation reaction is carried out at a temperature of 70~100° C. under a pressure greater than 1 atm.

Because acrylic acid is relatively easily condensed at a high temperature and has a boiling point of as relatively low as 141° C. under 1 atm, the condensation reaction is required to be conducted at a temperature of 110° C. or less under a pressure higher than 1 atm (preferably 1.05~3 atm) to prevent acrylic acid from being evaporated during the reaction. As a result, the effect obtained upon using excess acrylic acid is not diminished in the present invention. Consequently, a high production yield of 3-(hydroxyphenylphosphinyl)-propanoic acid is achieved in the present invention.

In addition, the relatively low temperature of the condensation reaction brings about significant reduction in by-products, compared with conventional high temperatures, thereby leading to the appearance of a desired color.

A better understanding of the present invention may be obtained in light of the following examples which are set forth to illustrate, but are not to be construed to limit the present invention.

EXAMPLE I

In a reactor were placed 895 g (5 moles) of phenylphosphonous dichloride, which was then heated at 80° C. with agitating. 396 g (5.5 moles) of acrylic acid were dropwise added while the reactor was maintained at a temperature of 80~100° C. under a pressure of 1.1 atm. Afer completion of the addition of acrylic acid, the reaction mixture was allowed to stand for 1 hour at 80° C. and then cooled to room temperature.

In 1,000 ml of water, the resulting reaction mixture was dropwise added and subjected to hydrolysis at 80° C., after which the temperature was cooled to near 10° C. to obtained precipitates. After being allowed to stand at 10° C. for 1 hour, the slurry containing the precipitates was filtered, washed and dried in a vacuum dryer to produce 1,015 g of 3-(hydroxyphenylphosphinyl)-propanoic acid. Yield 94.9%.

EXAMPLE II

Except using acrylic acid at an amount of 432 g (6 moles), the procedure of the Example I was repeated to allow 1,020 g of 3-(hydroxyphenylphosphinyl)-propanoic acid. Yield 95.3%.

Comparative Example I

The same procedure as in Example I was repeated except that 895 g (5 moles) of phenylphosphonous dichloride were placed in the reactor, heated to 80° C. with agitating, and dropwise added with 468 g(6.5 moles) of acrylic acid while maintaining a reaction temperature at 80~100° C. under 1 atm, to produce 998 g of 3-(hydroxyphenylphosphinyl)-propanoic acid. Yield 85.4%.

Comparative Example II

A procedure was carried out following Example I except that 895 g (5 moles) of phenylphosphonous dichloride were placed in the reactor, heated to 80° C. with agitating, and dropwise added with 386 g (5.35 moles) of acrylic acid while maintaining a reaction temperature at 80~100° C. under 1 atm, after which the reaction mixture was heated up to 130° C., allowed to stand for 1 hour, and cooled to room temperature, to produce 1,008 g of 3-(hydroxyphenylphosphinyl)-propanoic acid. Yield 94.2%.

The physical properties of 3-(hydroxyphenylphosphinyl)-propanoic acid obtained in the above examples are shown in Table 1, below.

TABLE 1

| Nos. of Examples | *Molar Ratio | Yield (%) | Color (L/b) | Melting Point (° C.) |
|---|---|---|---|---|
| I | 1.1 | 94.9 | 94.4/1.3 | 162 |
| II | 1.2 | 95.3 | 97.2/1.4 | 162 |
| C. I | 1.3 | 85.4 | 97.0/1.4 | 162 |
| C. II | 1.07 | 92.2 | 91.4/4.4 | 162 |

*moles of acrylic acid/moles of phenylphosphonous dichloride

As apparent in above Examples and Comparative Examples, 3-(hydroxyphenylphosphinyl)-propanoic acid can be prepared at high yields with good color, in accordance with the present invention. Therefore, the object material can be used as a flame retardant for polyester.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

We claim:

1. A method for preparing 3-(hydroxyphenylphosphinyl)-propanoic acid by the condensation of phenylphosphonous dichloride and acrylic acid and the hydrolysis of the condensate, in which, under a pressure of greater than 1 atm, acrylic acid is added at 65~110° C. at an amount more by 10~25 mole % than that of phenylphosphonous dichloride and the condensation is carried out at a temperature of 70~100° C. under a pressure greater than 1 atm.

2. The method as set forth in claim 1, wherein said the condensation reaction is carried out at a reaction pressure of 1.05~3 atm.

* * * * *